US007836894B2

(12) United States Patent
Brinkmann et al.

(10) Patent No.: US 7,836,894 B2
(45) Date of Patent: Nov. 23, 2010

(54) PHOTOTHERAPY METHOD FOR IRRADIATING BIOLOGICAL TISSUE WITH A SERIES OF LASER PULSE SEQUENCES

(75) Inventors: Ralf Brinkmann, Lübeck (DE); Georg Schuele, Menlo Park, CA (US)

(73) Assignee: Medizinisches Laserzentrum Luebeck GmbH, Luebeck (DE)

( * ) Notice: Subject to any disclaimer, the term of this patent is extended or adjusted under 35 U.S.C. 154(b) by 1303 days.

(21) Appl. No.: 11/327,939

(22) Filed: Jan. 9, 2006

(65) Prior Publication Data

US 2006/0111697 A1 May 25, 2006

Related U.S. Application Data

(63) Continuation-in-part of application No. PCT/DE2004/001498, filed on Jul. 9, 2004.

(30) Foreign Application Priority Data

Jul. 11, 2003 (DE) ................. 103 31 792

(51) Int. Cl.
*A61B 19/00* (2006.01)
(52) U.S. Cl. ................. 128/898; 607/88; 607/89; 606/9
(58) Field of Classification Search ........... 607/88–91; 606/4–6, 8, 9; 128/898
See application file for complete search history.

(56) References Cited

U.S. PATENT DOCUMENTS

| 5,302,259 | A | * | 4/1994 | Birngruber | 250/526 |
| 5,549,596 | A | * | 8/1996 | Latina | 606/4 |
| 5,549,632 | A | * | 8/1996 | Lai | 606/5 |
| 6,027,515 | A | * | 2/2000 | Cimino | 606/169 |
| 6,325,792 | B1 | * | 12/2001 | Swinger et al. | 606/4 |
| 6,464,692 | B1 | * | 10/2002 | Ruiz et al. | 606/5 |
| 6,610,052 | B2 | * | 8/2003 | Furumoto | 606/9 |
| 6,671,043 | B1 | | 12/2003 | Huettman | |
| 6,830,567 | B2 | * | 12/2004 | Schuele et al. | 606/4 |
| 2006/0111697 | A1 | * | 5/2006 | Brinkmann et al. | 606/4 |

FOREIGN PATENT DOCUMENTS

| DE | 39 36 716 A1 | 11/1989 |
| DE | 199 32 477 A | 2/2001 |
| DE | 199 32 477 A1 | 2/2001 |
| WO | WO 91/19539 A1 | 12/1991 |
| WO | WO 01/91661 A1 | 12/2001 |

* cited by examiner

*Primary Examiner*—Ahmed M Farah
(74) *Attorney, Agent, or Firm*—Larson & Larson P.A.; Frank Liebenow; Justin Miller (57) ABSTRACT

This invention relates to a method for operation of an irradiation laser whereby laser pulse sequences or pulses of varying length are modified during application such that the comparability of recorded transients is retained.

8 Claims, 5 Drawing Sheets

PHOTOTHERAPY METHOD FOR IRRADIATING BIOLOGICAL TISSUE WITH A SERIES OF LASER PULSE SEQUENCES

PRIOR APPLICATIONS

This US utility patent application is a continuation-in-part of PCT application number PCT/DE2004/001498, filed on Jul. 9, 2004 which bases priority on German application number DE 103 31 792.9, filed on Jul. 11, 2003.

BACKGROUND OF THE INVENTION

1. Field of Invention

The invention relates to a method for operating a laser. In particular, it relates to a method of operating a laser having dosimetry control for use in ophthalmic medicine, but also in general therapy of biological tissue.

2. Description of the Prior Art

In ophthalmology, laser systems are widely used both in correcting visual acuity (e.g. corneal ablation) and also in the therapy of retinal diseases. Lasers work well for this purpose due to the transparency of the eye for visible light.

Special interests exist in connection with the treatment of the dysfunction of "retinal pigmentary epithelium" (RPE), a highly pigmented monocellular layer between the choroid and retina of the eye. The highly multifunctional RPE, inter alia, governs the metabolism of photoreceptors, the liquid management of the retina and the phagocytosis of rhodopsin disks, the catabolites of the vision process. With increasing age, metabolic end products of constant receptor regeneration are accumulated in the RPE (inter alia lipofuscins), which leads to a continuously decreasing function of this cellular layer.

For example, senile macular degeneration (SMD) with rising incidence is the most frequent visual deprivation cause in people over 50 years old in industrial countries. According to the Framingham eye study, 2% of persons between the ages of 52 and 64 are affected by SMD, between 65 and 74 11%, and over a third of all people between the ages of 75 and 84 are affected with SMD. In the USA alone there was an estimate that there were 4 to 10 million patients in the year 2000.

The second most frequent cause of visual deprivation is diabetic retinopathy (DR), which is a late consequence of diabetes mellitus. With increasing duration of the disease, there is a rise in the frequency of retinal changes and after 30 years this rises to virtually 100%. Due to rises in human age, ever increasing importance is attached to early, efficient and careful therapy of SMD and DR. Retinal pigmentary epithelium is at least involved in the occurrence of SMD or DR, because vascularizations and edemas arise in the area round the RPE, which should not occur with a functionally intact RPE.

Fundamentally, no problems arise in the laser treatment of dysfunctional RPE, particularly in the early stage of the disease. Irradiation of targeted diseased areas of the eye fundus are admittedly thermally sclerosed and, as a result of the subsequent regeneration and lateral proliferation of RPE cells in the sclerotic zones, there are good prospects of a substantial restoration of the intact RPE. However, the production of temperatures lethal to the diseased cells through laser light absorption gives rise to potentially further damage to the surrounding tissue, which can lead to the necrosis of the non-regenerating photoreceptors and therefore to permanent loss of vision.

Selective RPE therapy (SRT), which by definition avoids damage to the RPE environment, is at present undergoing considerable development and has good prospects of establishing itself as a widespread therapy method in the near future. However, this presupposes that an optimized, easily handled laser system is marketed. The method of the present invention, inter alia, is intended to contribute to, and thus improve upon, such therapy.

According to the proposal of DE 39 36 716 C2, for the selective influencing of a good absorbing material in a matrix with a lower absorption capacity, repeat irradiation is recommended, such as the application of pulsed laser radiation. The rapidly succeeding arrival of a plurality of light pulses allows for heating of the target substance, which otherwise could only be obtained with a single pulse with a much higher energy. However, the time splitting of energy deposition, at the same time, allows for the utilization of heat and energy transport mechanisms in the material. The area heated in critical manner by the light is closely limited to the area around the target structures.

In the application of this concept to SRT, at present, a burst, i.e. a pulse sequence, of approximately 30 laser pulses with a pulse duration, in each case, of 1.7 µs in the green spectral range and with a pulse sequence rate of 100 Hz at a wavelength of 527 nm is used. Natural and numerous variations to these treatment parameters are also possible. For the thermotherapy of biological tissue, particularly of the eye fundus, clear preference is given to pulse durations of a few microseconds. The production of such laser pulses with an approximately constant pulse power is described in DE 44 01 917 C2. As a result of the strong pigmentation of the RPE (approximately 50% of the incident light in the green spectral range is absorbed by the pigment granules (melanosomes) in the RPE cells) high temperatures occur in the RPE in the case of corresponding irradiation (approx. 600 mJ/cmý per pulse), which lead to intracellular micro-vaporization on the strongly heated RPE melanosomes.

The resulting micro-bubbles for µs increase the cell volume and in all probability ultimately lead to the disruption and disintegration of the RPE cell. The irradiation threshold for cell damage can drop significantly through the application of multiple pulses.

A laser system for eye treatment which monitors the average pulse energy of the emitted radiation using sensors and controls the same by feedback, i.e. to a predefined value is described in WO 91/19539 A1. The intended protection of healthy cells is as little ensured with such a system as the therapeutic activity thereof. Thus, there is a considerable variation between patients concerning the prerequisites for laser therapy (e.g. transparency of the lens or glass body, pigmentation of the retina) in connection with eye fundus treatment.

Research results show that the necessary pulse energies for producing RPE effects fluctuate intra-individually by up to 100% and inter-individually to an even greater extent. Existing experience shows that the pulse energy must be no more than a factor of two above the threshold pulse energy for producing RPE damage, or otherwise visible damage occurs to the retina. However, a previously made choice regarding the laser energy for the same reason can be too low in order to influence the RPE, which renders the invention ineffective.

Checking the results of RPE damage can at present only take place after the end of treatment under clinical conditions. For dosimetry control, a fluorescence angiography of the eye fundus takes place after the operation. To this end, a dye (fluorescent or ICG) is injected into the bloodstream of the patient and diffuses from the choroid through the damaged RPE to the retina and in this way demarcates RPE defects during fundus fluorescence photography. However, this invasive procedure cannot be carried out in standard ophthalmic practices and consequently, at present, the therapy is restricted to well equipped clinics or university eye hospitals. Particularly with inadequate treatment results up to the decomposition of the dyes, there can be no direct continuation of the treatment and the fundamentally toxic action thereof often requires a long therapy interval. Thus, what is important for an effective, but protective treatment is the continuous observation of the radiation action on the tissue during the operation.

The already described destruction of RPE cells by thermal disruption forms the basis for DE 199 32 477 A1 C2 for the detection of RPE damage on the basis of mechanical deformations. The short-term expansion of irradiated RPE cells during the formation of gas bubbles (micro-vaporization) directly associated with RPE destruction can be acoustically measured and used for controlling a treatment laser. Below the pulse energy threshold necessary for bubble formation, the material response is thermo-elastic and reproducible, i.e. each incident pulse produces a pressure wave which, starting from the eye fundus, passes through the eyeball and as a function of time can be recorded with a transducer (e.g. an annular piezo-ceramic in a contact lens). Two successively applied, identical pulses produce identical pressure transients at the same material location. The amplitudes of the pressure transients are approximately linear to the pulse energy, provided that this remains below the bubble formation threshold.

On exceeding the threshold, the pressure amplitude rises in a super-proportional manner. The course of the transients changes between individual pulses, even with otherwise constant pulse shape and energy of the applied radiation due to the statistics of the use of micro-vaporization on melanin granules. In this way, the therapeutically effective pulse energy can be precisely determined and acts on the RPE cells, but leaves the surrounding area largely unaffected.

Initial treatments of patients have, in the meantime, shown that the opt-acoustic check is highly suitable to directly detect micro-vaporization on-line following laser burst application. Information up to now shows that the result is eminently correlated with the fluorescence angiographically established RPE leaks, in each case, determined following the treatment.

The resulting acoustic transients are measured with the aid of a sound transducer integrated into the contact lens. This does not impair the treatment, because contact lenses are in any case required for compensating the refraction of light of the eye media. The acoustic signals are pre-amplified, transferred to a PC and calculated.

The result in the form of a single number is indicated directly following the application of the burst and immediately informs the surgeon whether the pulse energy was adequate for RPE effects at the point just treated. If not, it is immediately possible to again apply a burst with a higher pulse energy.

A principal disadvantage of this procedure is its complicated nature, in that the surgeon may have to irradiate the same area with an increasing pulse energy until an RPE effect occurs. This also gives rise to the problem of the precise position of the application location on the retina. If a certain time elapses between the measurement of the energy requirement and the actual therapy irradiation, even minor eye movements can lead to therapy of the retina taking place at a different location. As a result of the aforementioned in homogeneity of the energy requirements for RPE damage, even in the eye of the same patient, this can cast doubts both on the success of the therapy and the avoidance of collateral damage. In addition, the irradiated area on the retina cannot be irradiated again, because the radiation application location is invisible to the surgeon, independently of the result of the irradiation, because an eye never remains stationary for more than a few seconds.

The optical detection of micro-vaporization on the retina is described in WO 01/91661 A1, use being made of the back-reflection of treatment or test laser light which increases with bubble formation.

Neither in WO 01/91661 A1 nor in the already cited DE 199 32 477 A1 are provided algorithms or information for controlling the treatment laser making it possible to treat all retina locations in the case of widely varying threshold values for RPE effects close to said threshold. It has been clinically shown that the threshold-near irradiation is absolutely necessary for selective RPE effects, because otherwise retinal damage occurs.

Initial results of research by the inventor have revealed that on individual patient treatment of energy thresholds between 200 and 350 µJ/pulse, the retinal damage thresholds (optical visibility of effects) are 300 µJ in areas with a low threshold. Thus, pulse energy leading to no effects in some areas, leads to visible retinal damage in other areas.

It is therefore desirable to carry out a control of the treatment laser in such a way that irradiation just above the threshold for RPE damage is possible in order to minimize the risks of serious side effects. Multiple radiation application per irradiation location is to be avoided. The surgeon should only have to irradiate once and needs to be sure that the desired RPE effects occur.

The task of searching for a therapeutically effective pulse energy no longer has to be carried out separately. It can reliably be assumed that the treatment is effective. This is particularly important for the widespread use of such treatment lasers in each ophthalmic practice, where the aforementioned methods for checking the results could not be performed other than with high costs or where the specialist would otherwise need special laser control training.

Therefore, the problem of the invention is to provide a method for operating an irradiation laser, in which laser pulse sequences or varying longer pulses, during application, are modified in such a way that the comparability of detected transients is maintained.

SUMMARY OF THE INVENTION

According to the present invention, a method is provided which formulates the bases for a machine-implement able laser control program. Advantageously, a laser with dosimetry control is used, which has a device for detecting thermally induced bubble formation in the irradiated tissue and for using the signal for controlling the laser. In a preferred embodiment, the bubble formation detection device can be either a pressure transducer or a piezo-ceramic pressure sensor for the pressure transient detection device. However, the bubble formation detection device can also be a photo-detector.

Particular suitability exists for lasers with an integrated compact fiber interferometer adapted to the ophthalmological application instrument.

An attenuating unit for rapidly reducing the laser power applied to the irradiated tissue, and located in the laser beam path, permits comparable conditions in connection with the detected transients.

In order to provide a method for operating a laser for applying a pulse sequence or a long pulse with stepwise increasing power, there must simultaneously be a detection of any micro-vaporization on the irradiated tissue, i.e. a bubble formation detection, which acts on the application of at least one further pulse sequence modified compared with the first sequence, following the initial bubble formation detection. The partial sequences or individual pulses must have, in each case, a duration between 0.05 and 50 microseconds and the applied power must be regulated by varying the duration of the individual pulses or the sequence rate thereof.

This gives rise to two possibilities for irradiating an area: 1) operating a laser by applying a long pulse of rising power covering the entire area while simultaneously detecting any micro-vaporization on the irradiated tissue and ending the pulse with a different power on detecting bubble formation; and 2) applying a lasting laser beam, which by means of deviating devices, produces a scanning pattern covering only a partial area of the tissue surface, while simultaneously detecting micro-vaporization of the irradiated tissue, and modulating the laser power in such a way that application takes place just above the bubble formation threshold.

For detecting bubble formation and the accompanying change, the reflectivity of the tissue is detected interferometrically via a modification to optical path lengths (refractive index). The investigated tissue is illuminated with a low power test light source, in particular a laser, which has a significantly different wavelength to that of the therapeutically effective laser pulse sequence, where at least one color filter upstream of the detector suppresses the detection of treatment light wave lengths. This test light beam advantageously follows the treatment light beam.

The method of the present invention proposes operating an irradiation laser which initially applies laser pulse sequences of finite duration (bursts). In each case, the pulse sequences include at least two time-succeeding applied partial pulse sequences of at least one pulse. A first partial pulse sequence starts from a predetermined, low pulse energy level and has a monotonically rising pulse energy. A second partial pulse sequence has a substantially constant pulse energy close to the end value of the first pulse sequence. Any bubble formation at the irradiation location is to be detected during the application of the first partial pulse sequence, which is ended. The second pulse sequence commences as soon as bubble formation is detected in the tissue.

However, it is also possible to use partial pulse sequences, so that working takes place with three partial pulse sequences of finite duration, in each case including at least three time-succeeding applied partial pulse sequences of, in each case, at least one pulse. The first partial pulse sequence has a constant pulse energy below the pulse energy threshold required for damaging the biological tissue. The second pulse sequence starts from the pulse energy level of the first partial pulse sequence and has a monotonically rising pulse energy. The third partial pulse sequence has a substantially constant pulse energy close to the end value of the second pulse sequence. Any bubble formation in the biological tissue at the radiation location is detected during the application of the first and second partial pulse sequences, so that an ending of the second pulse sequence and the commencement of the third pulse sequence takes place on a first detection of any bubble formation in the tissue. The third partial pulse sequence can comprise a plurality of pulses, whose pulse energy is just below the end value of the second partial pulse sequence.

Alternatively, the partial pulse sequence can have an initial constant pulse rate in such a way that the total energy applied per time unit is not sufficient to damage the biological tissue. The second partial pulse sequence can start from the pulse rate level of the first partial pulse sequence and can have a monotonically rising pulse rate. The third partial pulse sequence essentially has a pulse rate close to the end value of the second pulse sequence, so that a detection of any bubble formation in the biological tissue at the irradiation location takes place during the application of the first and second partial pulse sequences. And if so, a termination of the second pulse sequence and a commencement of the third pulse sequence takes place as soon as such bubble formation is first detected in the tissue.

A measurement or test signal indicating bubble formation during the first partial pulse sequence should be recalibrated for each irradiation location and the laser pulse sequences advantageously have pulse durations between 0.05 and 50 microseconds.

However, there is also a detection of the application of a continuously emitting laser beam, successively deflected onto a plurality of irradiation locations on the biological tissue by means of a controllable deflector. The deflection of the laser beam is periodically repeatable if any bubble formation is detected in the biological tissue at the irradiation locations during a monotonic rise of the laser power. There is also a reduction of the laser power, after a predetermined action time, starting as soon as any bubble formation is detected in the tissue.

The emitted laser power is to be attenuated externally of the resonator or increased by reducing attenuation. This attenuation can e.g. take place by controlling a polarizer.

The method for operating a biological tissue-irradiating laser can also take place by applying a single laser pulse with a pulse duration of up to 50 microseconds and whose pulse energy rises monotonically during a first time period of its emission and remain substantially constant during a second time period of its emission. This is followed by detection of any bubble formation in the biological tissue at the irradiation location during the first time period of laser pulse emission and cutting off the laser pulse following a predetermined action time starting as soon as any bubble formation is detected in the tissue.

The laser pulse is to be produced with a Q-switched laser allowing a pulse shape control or check, permitting bubble formation detection in the tissue by the recording of pressure transients passing through the tissue and emanating from the bubble formation location, or an accompanying change to the reflectivity of the tissue. However, it is also possible to detect bubble formation interferometrically by means of a change to optical path lengths (refractive index). This can take place by illuminating the investigated tissue with a low power test light source, particularly a laser, which has a significantly different wavelength to that of the therapeutically active laser. A color filter upstream of the detector is intended to suppress the detection of treatment light wave lengths.

It is proposed that the test light be deflected with the same deflector as the treatment light, in that the illumination location of the test light follows the irradiation location of the treatment light.

BRIEF DESCRIPTION OF THE DRAWINGS

The detailed description of the invention, contained herein below, may be better understood when accompanied by a brief description of the drawings, wherein.

DETAILED DESCRIPTION OF THE PREFERED EMBODIMENT

Figure 1:
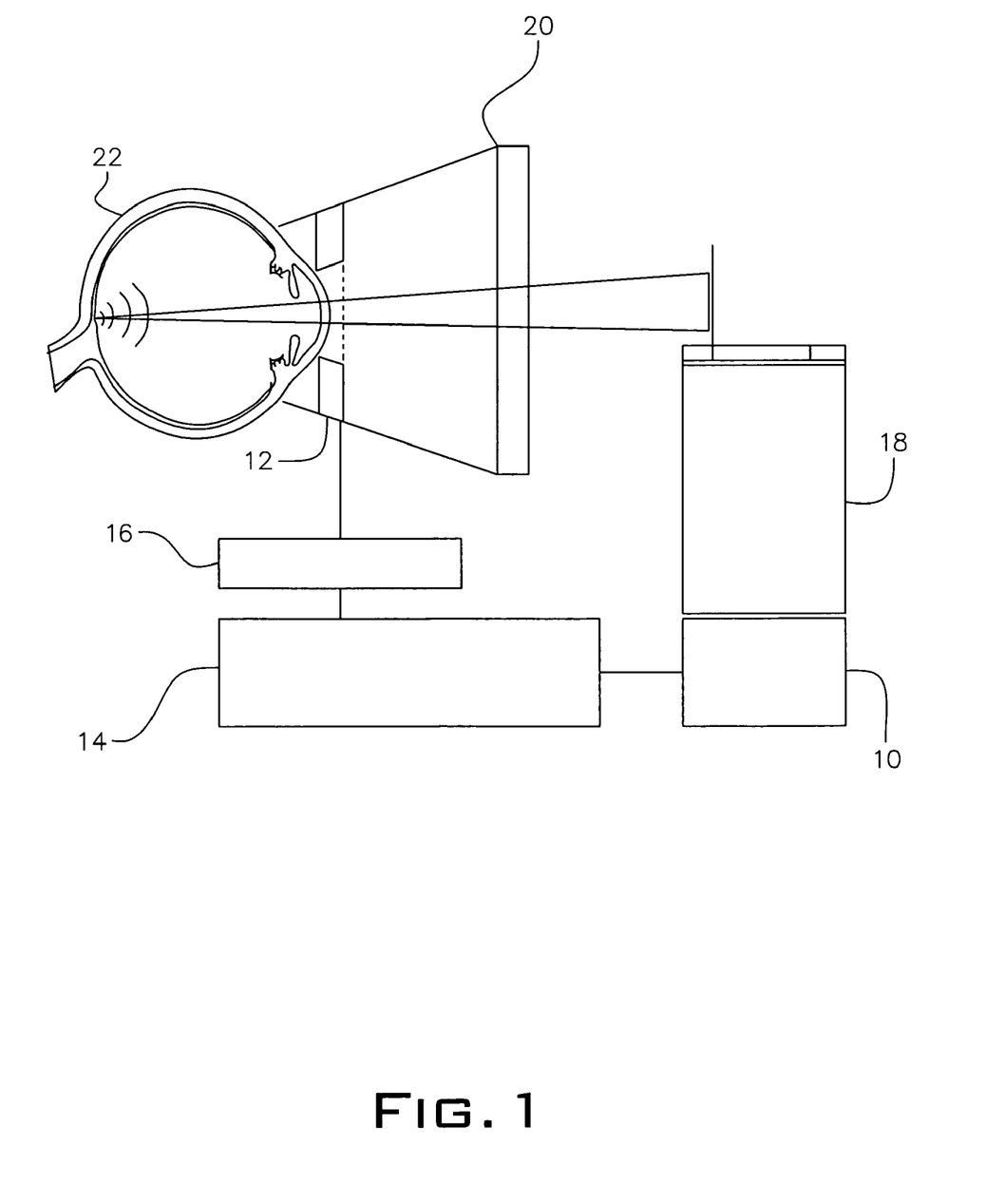
FIG. 1 is a survey sketch of an embodiment for an opto-acoustic measurement on an eye.

FIG. 1 shows an ophthalmological treatment system having three components, namely a laser 10, a detection unit 12 for measuring the irradiation action in the tissue and an evaluation and control unit comprising at least one programmable microprocessor 14, particularly a PC, and usually also an amplifier 16 for detecting signals. Reference numeral 18 designates a slot lamp, 20 designates an opto-acoustic contact lens, while 22 designates an eye to be treated.

Specifically FIG. 1 provides for the measurement of pressure transients with a piezo-detector 12 of lead zirconium titanate (LZT), because safe findings already exist for this structure. It is understood that a piezo-detector fabricated from other materials could be employed.

In principle, numerous alternative methods are conceivable for detecting bubble formation in the irradiated tissue and more particularly, purely optical methods are preferred. Thus, e.g. during bubble formation there is a significant change to tissue reflectivity if additional liquid/gas phase interfaces appear for the first time. This can be established by directly measuring the reflected light intensity, use preferably being made of a low power test laser parallel to the treatment laser. Preferably, both lasers emit different wavelengths, so that by means of a color selective filter only the test light, which is minimally absorbed by the tissue, reaches detector unit 12 (photoreceptor, e.g. CCD).

Another possibility is for the interferometric measurement of bubble formation, in which the laser light transit time within the RPE cellular layer is determined. The occurrence of gas bubbles significantly changes the refractive index of the layer. Light backscattered from the two interfaces of the typically 300 μm RPE layer has a path difference, whose change is detected with an interferometer.

Hereinafter, the explanation of the method of the present invention is limited to opto-acoustic tissue response, i.e. to recordable pressure transients.

Figure 2A:
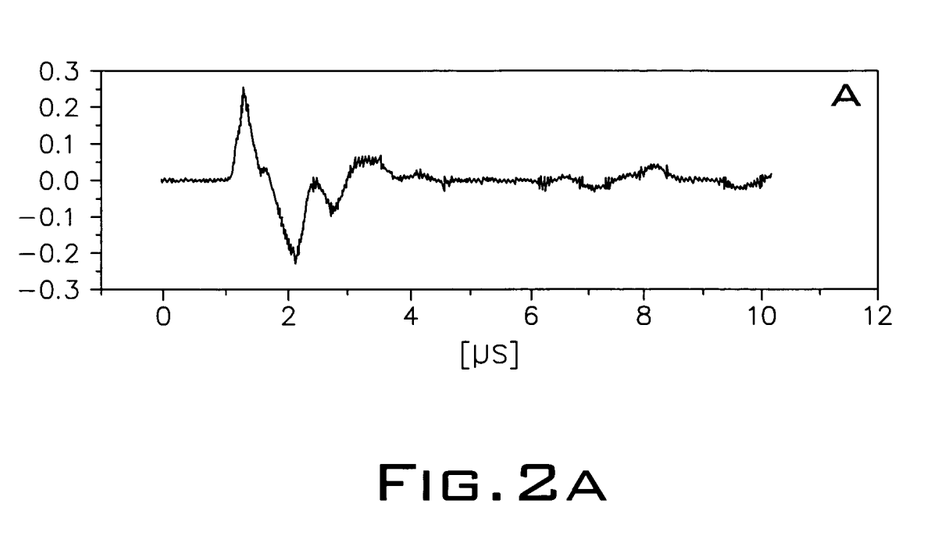
FIG. 2 is illustrates measurement results in a curve form wherein the superimposing of pressure transients of from pulse energy below a bubble formation threshold (A) and then pulse energy above a bubble formation threshold (B); time being plotted on the x axis and pressure being plotted in random units on the y axis (for both (A) and (B), thirty traces)
Figure 2B:
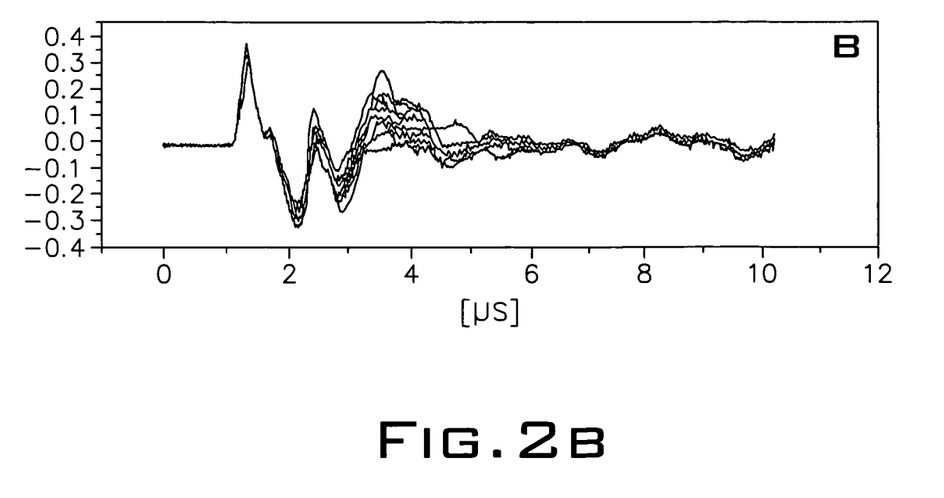

FIGS. 2A and 2B both illustrate the superimposing of 30 recorded pressure transients for 30 uniform laser pulses emitted during a laser burst. If the pulse energy is below the bubble formation threshold, all the transients have substantially the same path as shown in FIG. 2(A). The reason for this is the thermo-elastic expansion property of the tissue under irradiation; the tissue returns to its initial state at the termination of each pulse. As shown in FIG. 2A, there is no significant change to the transient path on using higher pulse energies, but still below the threshold.

It is recommended that the measured amplitudes of the transients be, in each case, divided by the pulse energy. In this way, the electrical test signal is standardized for different pulse energies. However, if the pulse energy is sufficient for bubble formation, the statistical character of the vaporization leads to a different path for the transients between individual pulses, even if the pulses always have the same features, as illustrated by FIG. 2B. After the burst, it is possible to, establish using standard computer analysis from the characteristic of the group of test signals, whether there has or has not been RPE damage due to thermal disruption.

To render superfluous multiple application of laser radiation to the same retinal location, the inventive laser system is designed to modify and substantially raise the pulse energy within a single burst. With the aid of the aforementioned standardization of the signals, it is possible to carry out in a continuous manner, and in real time, signal comparison for following pulses of differing energy. This data can then be used for deciding whether the next pulse should or should not have a somewhat higher energy level. The requisite signal processing speed no longer causes problems in view of modern GHz processors.

The varying of the pulse energy is preferably implemented by resonator-external attenuation of the treatment light in an attenuation unit. Thus, the generally polarized laser radiation can be darkened in a controlled manner by a second polarizer adjustable by the control unit and which is followed by a fixed polarization beam splitter. Electrical, switchable polarizers having adequate switching speed and precision are available, e.g. Pockels cells. It is also possible to use acousto-optical modulators, which operate in a polarization-independent manner.

It must once again be stressed here that a change to the pulse energy by regulating the pumping power is disadvantageous, because it generally also influences the pulse shape, which can only be avoided through complicated electronics. On changing the pulse shape, the pressure transients will, in each case, have different paths, even if there is no bubble formation.

Numerous strategies are conceivable as to the way in which the pulse energy is to be adapted to the measurement findings (micro-vaporization affirmed or not). For reasons of simplicity, it is assumed hereinafter that signal evaluation and energy regulation in each case take place between two individual pulses. This is certainly a preferred implementation of the method, but in principle in place of individual or single pulses account can also be taken of multi-pulse partial sequences of the complete laser burst per adaptation cycle.

FIG. 3 show, in an exemplified graphical form, a selection of control or regulating strategies for the pulse energy sequences to be employed. FIGS. 3a-e, in each case, illustrate repeat pulsed irradiation. FIG. 3f illustrates a single pulse irradiation and FIG. 3g a scanning application. The downward arrow (↓) in each figure marks a pulse where bubble formation has been detected, while any upward arrow (↑) marks the time where there is no further micro-bubble measurement.

It is common to all the strategies that a monotonically rising laser power ramp is tracked and this only ends when micro-vaporization occurs. For example, in strategy A (FIG. 3a), after detecting vaporization, a further pulse with a somewhat higher energy is applied in order to reliably bring about the therapeutic action. Thereafter, the burst is terminated.

Strategy B (FIG. 3b) commences with a multiple, low energy pulse sequence in order to find a better basic signal below the bubble threshold and, from which it is possible, to derive in a reliable manner the threshold energy. The burst conservatively ends at the first sign of gas bubbles; Strategy B represents maximum caution.

Strategy C (FIG. 3c) has maximum effectiveness, in that the first pulse with micro-vaporization is followed by a series of further pulses with the same energy level.

Strategy D (FIG. 3d) is somewhat more cautious, in that the pulse energy is slightly reduced following the threshold pulse (arrow). This corresponds to the finding that, in the case of repeat irradiation, therapeutic damage can be brought about with lower pulse energies than in the case of single pulses.

In strategy E (FIG. 3e) the pulse power is kept constant, but the average power is raised by increasing the pulse sequence rate. In a targeted manner, the RPE is heated somewhat, so that the remaining pulse energy leading to the vaporization temperature becomes ever smaller. On reaching this, the pulse sequence rate is kept constant. This solution is particularly characterized by its simple implementation, because only the frequency generator has to be controlled and no fast high voltage electronics are required. Measurements have revealed that the pulse shape and energy up to pulse sequence rates of 500 Hz remain unchanged.

The strategies above described can be implemented without control unit microelectronic costs and can be stored there in parallel as selectable options, which can be polled by the surgeon by pressing a button.

Further developments can exist with regards to the nature of the power rise, which is e.g. linear in FIGS. 3a-d. It is also possible to have a geometrical progression (e.g. a rise by 5% in each case) in the power without any further growth specification, provided that the threshold energy is not exceeded.

On implementing strategies C or D, it can also be appropriate to have the same number of therapeutically active pulses after reaching the vaporization threshold during each burst and, in particular, following a pre-programmed setting by the treating specialist.

The preferred embodiment of the controlled laser system comprises a Q-switched laser, which upon activation emits a pulse sequence of variable pulse energy with a pulse duration of a few microseconds. Half a microsecond roughly corresponds to the thermal relaxation time of irradiated melanosomes, 50 µs roughly that of the RPE, i.e. the local heating produced by irradiation in shorter application times than the relaxation time leads to no significantly increased temperatures which could bring about damage to the adjacent tissue.

Figure 3A:
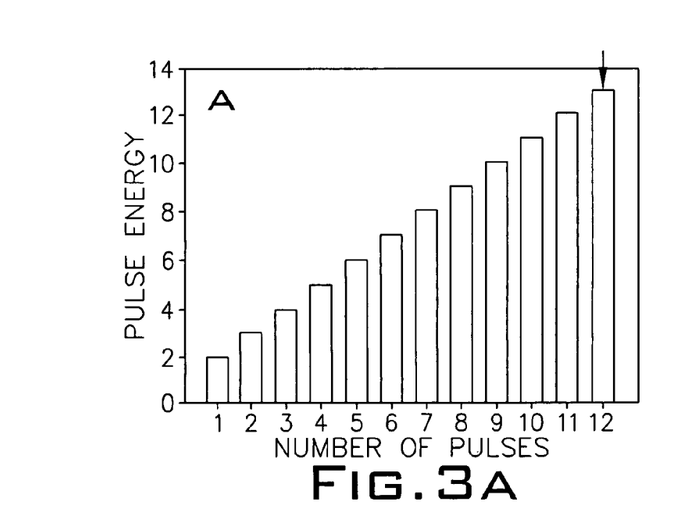
FIG. 3a shows an example for a rising pulse energy sequence until there is bubble formation detection.
Figure 3B:
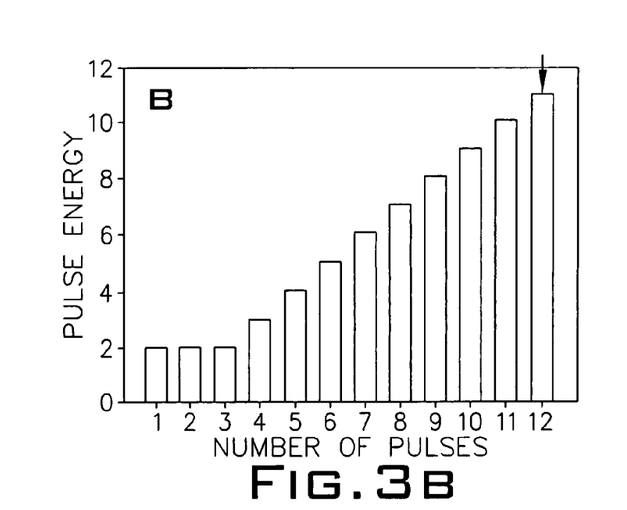
FIG. 3b shows another example for a rising pulse energy sequence until there is bubble formation detection.
Figure 3C:
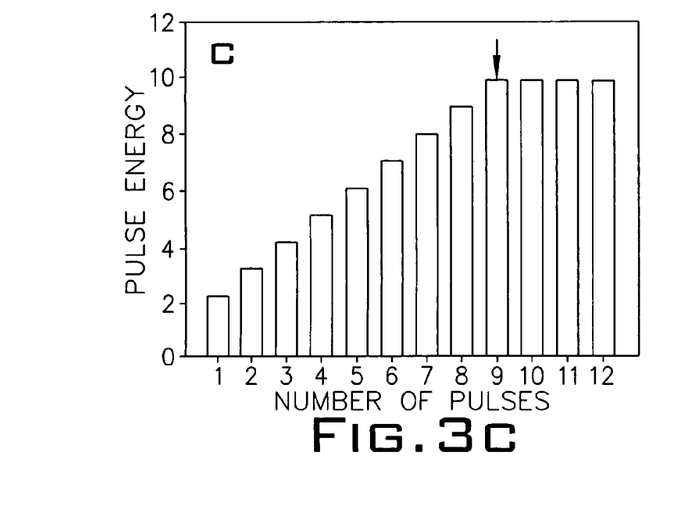
FIG. 3c shows an example of no further pulse energy rise once there has been bubble formation detection.
Figure 3D:
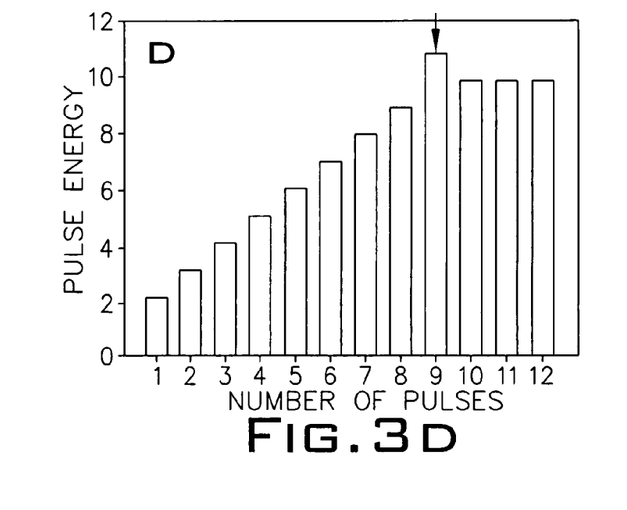
FIG. 3d shows an example of a reduced pulse energy sequence once there has been bubble formation detection.
Figure 3E:
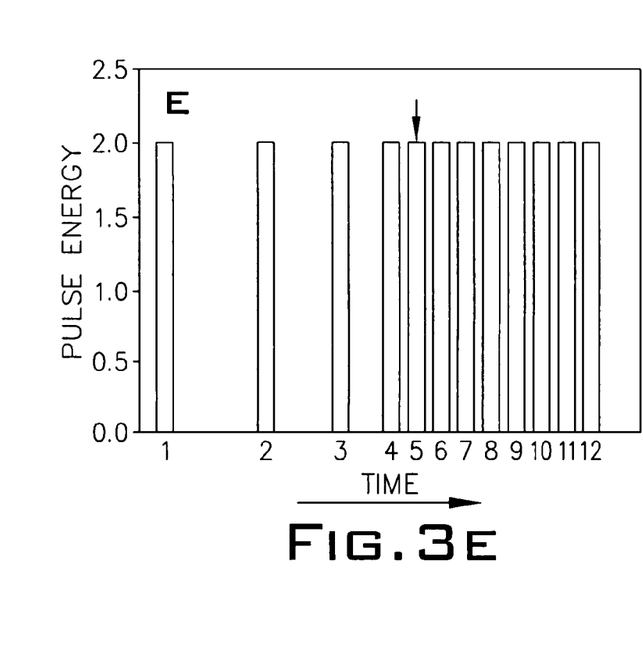
FIG. 3e shows an example for a change to the pulse energy spacing in a sequence (the time between bursts), once there has been bubble formation detection.
Figure 3F:
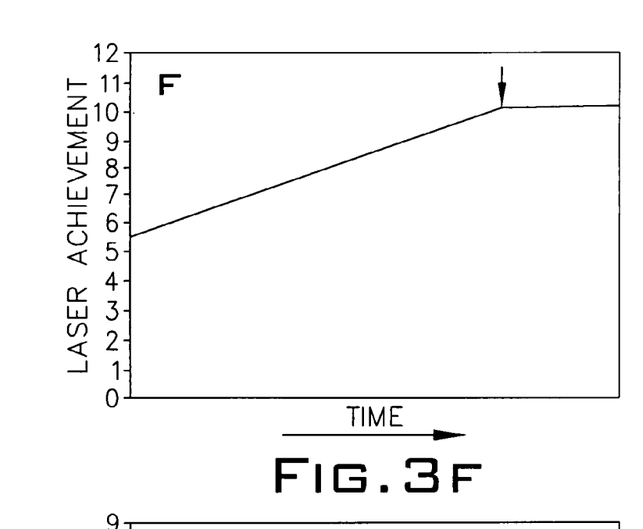
FIG. 3f shows an example of a single pulse irradiation over time.

Thus, even a longer single pulse, e.g. lasting 50 µs can bring about the careful, protective therapy effect, if the pulse power only rises during its emission, in accordance with the above strategies (FIG. 3f). It is important to switch off the long pulse shortly after bubble formation occurs. The energy ramp is then again followed for each single pulse. Reference to the optical proof is indicated for respective detection of micro-vaporization.

Another embodiment of the invention includes a continuous wave or CW laser, whose light is deflected in a controlled manner using an opto-acoustic deflector and guided in a scanning manner over the entire retina. The scanning rate of the scanner determines the repetition rate of the quasi-pulsed light at each point of the retina. The light of a second, low power test laser is deflected by the modulator in a manner that its impact point on the retina directly follows that of the treatment laser. The treatment laser power is increased during the scan until bubble formation can be detected by means of the backscattered treatment or test light. The treatment power is then lowered again after a short time until no further bubble formation is detected and the ramp rise starts afresh.

Figure 3G:
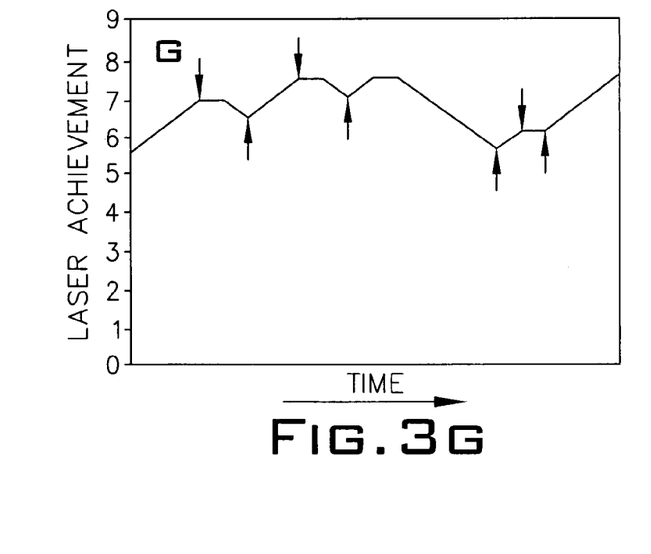
FIG. 3g shows an another example of a single pulse irradiation over time.

A possible strategy in this connection is shown in FIG. 3g. The pulse power at the treatment laser output consequently corresponds to an irregular saw-tooth function modulated by feedback. Obviously, numerous other variants of this structure are possible.

Figure 4:
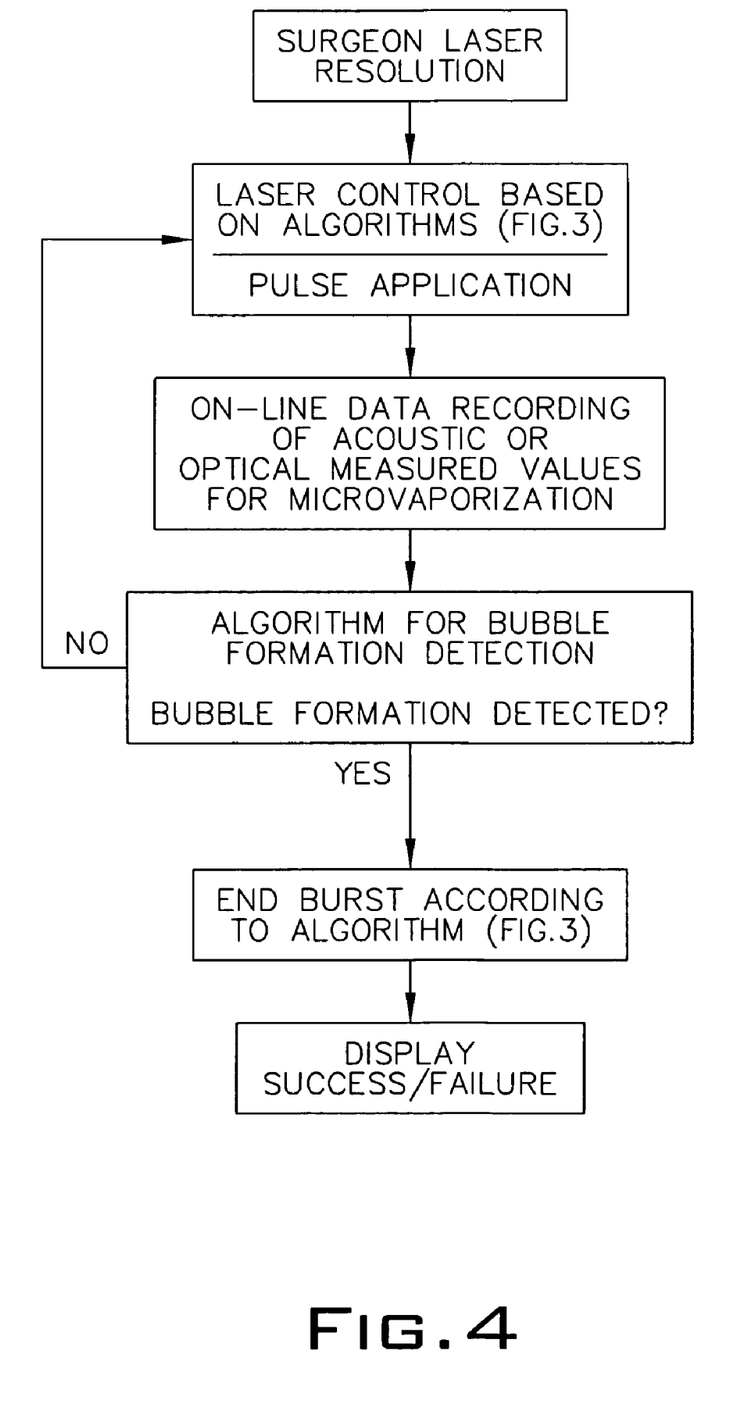
FIG. 4 is a flow diagram illustrating the procedural steps carried out in the method of the present invention.

The above-described method guarantees through the measurement detection of tissue vaporization that, in the case of laser-assisted thermotherapy, the planned tissue damage, particularly on the eye fundus, occurs when pulsed laser radiation is applied. At the same time, the proposed control specification using the example of repeat pulsed irradiation (see flow chart FIG. 4) ensures that the laser system automatically seeks and uses the minimum laser power required. Similar algorithms can also be used for single pulse or scanning irradiation.

When applied to retinal pigmentary epithelium (RPE), the method of the present invention avoids damage to cells that are not to be treated, particularly photoreceptors, without any active intervention on the part of the surgeon for dosimetry control purposes.

The laser used is consequently provided with a dosimetry control for emitting time-limited laser light controlled by a device for detecting thermally induced bubble formation and the accompanying density fluctuations and reflectivity changes in the irradiated tissue. This density fluctuation can be opto-acoustically detected by a sound transducer. A piezo-ceramic pressure sensor is particularly suitable.

For the detection of density fluctuations that modify the reflectivity of the tissue, it is possible to opto-acoustically detect the intensity change (refractive index) in a direct manner using a photodiode, followed by evaluation. The rise in the bubble can be interferometrically detected via a change to the optical path lengths, which offers the advantage of stray light suppression from the eye and provides additional information concerning the size and extension of the bubble.

For rapid power control, the laser beam path preferably contains a beam attenuation unit, particularly for rapidly reducing the laser power applied to the irradiated tissue. Alternatively, and in the case of repeat irradiation, the applied average power can be modulated via the pulse sequence rate.

The present inventive method for operating a pulsed laser consequently involves the following: application of pulse sequences with stepwise rising power and simultaneous detection of any micro-vaporization on the irradiated tissue and application of further pulse sequences with substantially the same power as that at which bubble formation was first detected. Preferably, all partial pulse sequences are of the same length and preferably include individual pulses, the partial sequence or individual pulses each having a duration between 50 nanoseconds and 50 microseconds.

The laser with dosimetry control can also be provided with a photo-detector for bubble formation detection, or there can even be a detector row and light guide for building up an integrated interferometer. Preference is given to compact fiber interferometers adapted to the ophthalmological application instrument.

On illuminating the investigated tissue for detecting bubble formation using a low power test light source, particularly a laser, which has a significantly different wavelength to that of the therapeutically active laser pulse sequence, the detection of treatment light wave lengths can be suppressed by means of a color filter upstream of the detector.

In place of a pulse sequence, it is also possible to use a long pulse with continuously rising power while simultaneously detecting any micro-vaporization on the irradiated tissue, the pulse being terminated on detecting any micro-vaporization.

It is also possible to use a CW laser, whose light is deflected in a controlled manner with the aid of e.g. an opto-acoustic deflector and which is guided in a scanning manner over the entire retina, the power emitted being varied in a substantially saw-tooth manner. The micro-vaporization preferably takes place optically by means of reflected light of the treatment laser or a wavelength-differing test laser, which illuminates the micro-vaporization affected area.

Equivalent elements or steps can be substituted for ones set forth herein to achieve the same results in the same way and in the same manner.

Having thus described the present invention in the detailed description of the preferred embodiment, what is desired to be obtained in Letters Patent is:

1. A method for operating a biological tissue-irradiating laser on an irradiation location of tissue, the steps of the method comprising:
   a) applying a series of laser pulse sequences of finite duration, each laser pulse sequence of said series having at least two time-succeeding applied partial pulse sequences, each at least two time-succeeding applied partial pulse sequences having at least one pulse, said at least two time-succeeding applied partial pulse sequences comprising a first and second partial pulse sequence, said first partial pulse sequence starting from a pre-determined, low pulse energy level and having a monotonically rising pulse energy level, and said second partial pulse sequence having a substantially constant pulse energy level near an end value of said first partial pulse sequence rising energy level;
   b) detecting bubble formation at said irradiation location during application of said first partial pulse sequence; and
   c) ending said first partial pulse sequence and commencing said second partial pulse sequence immediately upon detection of said bubble formation in said tissue.

2. The method according to claim 1, wherein said second partial pulse sequence comprises a plurality of pulses, said plurality of pulses having a pulse energy level slightly below that of said end value of said first partial pulse sequence rising energy level.

3. The method according to claim 1, further comprising the step of recalibrating a test signal for detecting bubble formation during said first partial pulse sequence.

4. The method according to claim 1, wherein each laser pulse sequence of said series has a pulse duration between 0.05 and 50 microseconds.

5. The method according to claim 1, wherein said series of laser pulse sequences comprises at least one laser pulse sequence.

6. The method according to claim 5, wherein said at least one laser pulse is subjected to a pulse shape check by as Q-switched laser.

7. The method according to claim 5, wherein the step of detecting bubble formation is accomplished by detecting a phase change to a reflected signal of said at least one laser pulse.

8. The method according to claim 5, wherein the step of detecting bubble formation is accomplished by interferometrically detecting a change in an optical path length of said at least one laser pulse.

* * * * *